(12) United States Patent
Riemann et al.

(10) Patent No.: US 8,501,035 B2
(45) Date of Patent: Aug. 6, 2013

(54) ABSORPTION MEDIUM FOR REMOVING ACID GASES FROM A FLUID STREAM

(75) Inventors: Christian Riemann, Altrip (DE); Torsten Katz, Neustadt (DE); Georg Sieder, Bad Dürkheim (DE); Gerald Vorberg, Speyer (DE); Erika Dengler, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 381 days.

(21) Appl. No.: 12/850,041

(22) Filed: Aug. 4, 2010

(65) Prior Publication Data
US 2011/0033354 A1 Feb. 10, 2011

(30) Foreign Application Priority Data
Aug. 4, 2009 (EP) .................... 09167181

(51) Int. Cl.
- C07C 229/12 (2006.01)
- C07D 241/04 (2006.01)
- B01D 53/40 (2006.01)

(52) U.S. Cl.
USPC ........... 252/184; 562/553; 562/575; 544/404; 423/210; 423/220; 423/226; 423/228

(58) Field of Classification Search
USPC ... 252/184; 423/210, 220, 226, 228; 562/553, 562/575; 560/155; 544/404
See application file for complete search history.

(56) References Cited

U.S. PATENT DOCUMENTS
| | | |
|---|---|---|
| 2004/0253159 A1 | 12/2004 | Hakka et al. |
| 2006/0138384 A1 | 6/2006 | Grossman et al. |

FOREIGN PATENT DOCUMENTS
| | | |
|---|---|---|
| CA | 02651696 | 11/2007 |
| DE | 10306254 | 8/2004 |
| EP | 671200 | 9/1995 |
| EP | 1806171 | 7/2007 |
| WO | WO-2007/135028 A1 | 11/2007 |
| WO | WO 2008/155394 | * 12/2008 |
| WO | WO-2009/156271 A1 | 12/2009 |
| WO | WO-2009/156273 A1 | 12/2009 |

\* cited by examiner

*Primary Examiner* — Stanley Silverman
*Assistant Examiner* — Daniel Berns
(74) *Attorney, Agent, or Firm* — Novak Druce Connolly Bove + Quigg LLP

(57) ABSTRACT

An absorption medium for removing acid gases from a fluid stream comprises an aqueous solution (A) of an alkali metal salt of an N,N-di-$C_1$-$C_4$-alkylaminocarboxylic acid and (B) N-hydroxyethylpiperazine. The absorption medium has a low vapor pressure and an increased resistance to oxygen. Preferred fluid streams are combustion exhaust gases or biogas.

24 Claims, 1 Drawing Sheet

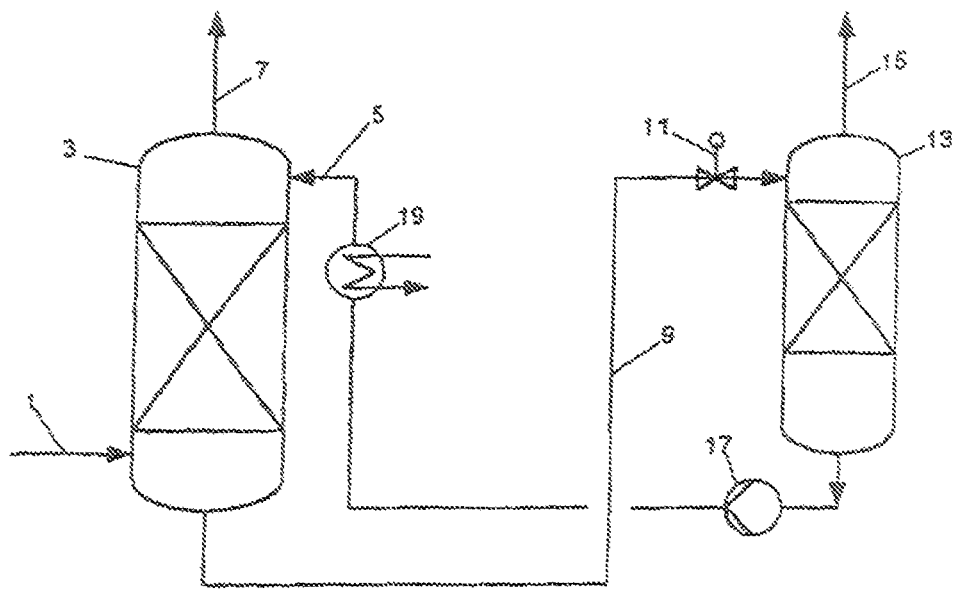

ABSORPTION MEDIUM FOR REMOVING ACID GASES FROM A FLUID STREAM

CROSS REFERENCE TO RELATED APPLICATIONS

This application claims benefit of European application number 09167181.84, filed Aug. 4, 2009, the entire content of which is hereby incorporated by reference.

The present invention relates to an absorption medium and a process for removing acid gases from a fluid stream, in particular an oxygen-comprising fluid stream.

The removal of acid gases such as, e.g. $CO_2$, $H_2S$, $SO_2$, $CS_2$, HCN, COS or mercaptans, from fluid streams is of importance for varied reasons.

The removal of carbon dioxide from combustion exhaust gases or flue gases is desirable for various reasons, but in particular for reducing the emission of carbon dioxide which is considered to be the main cause of what is termed the greenhouse effect.

The removal of carbon dioxide and hydrogen sulfide from biogas is used for methane enrichment in order to work up the biogas to natural gas quality.

The content of sulfur compounds in natural gas must be reduced by suitable workup measures directly at the natural gas well, since the sulfur compounds, in the water which is frequently entrained by the natural gas, form acids which are corrosive. Therefore, for the transport of natural gas in a pipeline, predetermined limiting values of the sulfur-comprising impurities must be complied with. Reducing the content of carbon dioxide is widely required for setting a predetermined calorific value.

For the removal of acid gases, frequently scrubbers are used having absorption media in the form of aqueous solutions of organic amines. When acid gases are dissolved in the absorption medium, ions form with the amines. The absorption medium can be regenerated by expansion to a lower pressure and/or by stripping, wherein the ionic species back react to form acid gases and/or are stripped off by means of steam. After the regeneration process, the absorption medium can be reused.

In particular in the case of scrubbing operations which are carried out at low pressure close to atmospheric pressure, amines which have a comparatively high vapor pressure can pass over into the clean gas. For avoidance of unwanted emissions, the clean gas obtained after the amine scrubbing must be subjected to a further scrubbing with water.

Certain problems occur in the treatment of acid-comprising fluids, e.g. flue gases. In this case the absorption capacity of the absorption medium becomes impaired in the long term and is not completely recovered in the regeneration. The presence of molecular oxygen is suspected to be responsible for an oxidative decomposition of the amines present in the absorption medium. For avoidance of this problem it has already been proposed to add to the absorption medium stabilizers against the oxygen-induced decomposition. Although the use of stabilizers effectively suppresses the decomposition of the amines, their use is associated with considerable cost, since the amount of stabilizer must be constantly supplemented.

EP-A 671 200 describes a process for removal of carbon dioxide from combustion exhaust gases, in which the combustion exhaust gas is contacted with an aqueous solution of an amino acid metal salt and piperazine. Amino acid metal salts illustrated are potassium dimethylaminoacetate and potassium α-methylaminopropionate.

EP-A 1 806 171 discloses a process for obtaining $SO_2$ and $CO_2$ from a gas stream. An absorption medium is used which comprises at least one tertiary amine and at least one secondary amine as activator. Examples of activators are N-hydroxyethyl-piperazine, piperazine and N-hydroxypropylpiperazine.

US 2004/0253159 discloses a process for obtaining $CO_2$ from a gas stream. An absorption medium is used which comprises at least one tertiary amine having a pKa of 6.5 to 9. The absorption medium optionally comprises a secondary amine. Examples of secondary amines are N-hydroxyethylpiperazine, piperazine and N-hydroxypropyl-piperazine.

DE 103 06 254 describes an absorption medium for the removal of acid gases from fluids which comprises at least one tertiary alkanolamine and an amine which is selected from hydroxyethylpiperazine, bis(hydroxyethyl)piperazine or a mixture thereof.

WO 2007/135028 describes a process for removing acid gases from a hydrocarbonaceous fluid stream or an oxygen-comprising fluid stream, in which the fluid stream is contacted with an aqueous solution which comprises at least one amine and at least one metal salt of an aminocarboxylic acid and/or aminosulfonic acid.

The object of the invention is to specify an absorption medium for removing acid gases from a fluid stream, the components of which are different from water have a low vapor pressure and which absorption medium has an increased resistance to oxygen.

The object is achieved by an absorption medium for removing acid gases from a fluid stream, which absorption medium comprises an aqueous solution
(A) of an alkali metal salt of an N,N-di-$C_1$-$C_4$-alkylaminocarboxylic acid and
(B) N-hydroxyethylpiperazine.

The invention additionally relates to a process for removing acid gases from a fluid stream, in which the fluid stream is contacted with the abovedefined absorption medium.

The alkali metal salt of the N,N-di-$C_1$-$C_4$-alkylaminocarboxylic acid possesses a tertiary amino group. Whereas primary and secondary amines form soluble carbamates with carbon dioxide, tertiary amino groups do not react directly with carbon dioxide, since the nitrogen atom is completely substituted. Rather, carbon dioxide reacts with the tertiary amine and water to form bicarbonate in a reaction having a low reaction rate. Since no direct bond is formed between tertiary amines and carbon dioxide, the amine solution can be regenerated very economically. However, a disadvantage of the use of tertiary amine solutions is that, because of the low reaction rate of carbon dioxide, the scrubbing process must be carried out using a very long residence time. The absorption rate of carbon dioxide into aqueous solutions of tertiary amines can be increased by the addition of further compounds which are termed activators or promoters. Primary or secondary amines are suitable activators. In the absorption medium according to the invention, the N-hydroxyethylpiperazine has the function of an activator.

The absorption medium according to the invention having N-hydroxyethylpiperazine as activator achieves comparable absorption performances as comparative absorption media having the same molar concentrations of piperazine. However, it has been found that N-hydroxyethylpiperazine is unexpectedly stable in the presence of oxygen, whereas piperazine which, as does N-hydroxyethylpiperazine, comprises secondary amino group(s), decomposes rapidly in the presence of oxygen.

The alkali metal salt of N,N-di-$C_1$-$C_4$-alkylaminocarboxylic acid, as a salt-type compound, has virtually no vapor pressure. It exhibits an excellent stability against oxygen even at elevated temperatures.

The aqueous solution generally comprises 2 to 5 kmol/m', preferably 2.3 to 3.3 kmol/m$^3$, of alkali metal salt of the N,N-di-$C_1$-$C_4$-alkylaminocarboxylic acid; it generally comprises 0.1 to 1.5 kmol/m$^3$, preferably 0.5 to 1.2 kmol/m$^3$, of N-hydroxyethylpiperazine.

Aminocarboxylic acids comprise at least one amino group and at least one carboxyl group in their molecular structure. If the aminocarboxylic acid has one or more chiral carbon atoms, the configuration is of no importance; not only the pure enantiomers/diastereomers but also any desired mixtures or racemates can be used.

The aminocarboxylic acid is preferably an α-amino acid or a β-amino acid. Of these. α-amino acids are particularly preferred. The designation "α" or "β" means, in agreement with the conventional nomenclature, that the amino group is separated from the carboxyl group by one or two carbon atoms, respectively.

Suitable alkali metal salts of an N,N-di-$C_1$-$C_4$-alkylaminocarboxylic acid are, for example, alkali metal salts of N,N-dimethylglycine (dimethylaminoacetic acid), N,N-diethylglycine, N,N-dimethylalanine, N,N-dimethylleucine, N,N-dimethylisoleucine, N,N-dimethylvaline and N,N-dimethylserine.

The alkali metal salt is generally a sodium and/or potassium salt, preferably a potassium salt.

A preferred alkali metal salt of an N,N-di-$C_1$-$C_4$-alkylaminocarboxylic acid is potassium N,N-dimethylglycinate.

The absorption medium can also comprise additives, such as corrosion inhibitors, enzymes etc. Generally, the amount of such additives is in the range of about 0.01-3% by weight of the absorption medium.

The acid gases which can be removed using the absorption medium according to the invention include carbon dioxide, $H_2S$, SOS, $SO_2$, $CS_2$, HCN, COS, disulfides and mercaptans. Generally the acid gases comprise at least carbon dioxide and optionally other acid gases. For instance, the acid gases to be removed can comprise, e.g. carbon dioxide and $H_2S$, or carbon dioxide and $SO_2$.

The process or absorption medium according to the invention is suitable for treating fluids of all types. Fluids which comprise the acid gases are firstly gases, such as natural gas, synthesis gas, coke oven gas, cracked gas, coal gasification gas, cycle gas, landfill gases and combustion exhaust gases, and secondly fluids which are essentially immiscible with the absorption medium, such as liquefied petroleum gas (LPG) or natural gas liquids (NGL).

Owing to the excellent resistance of the absorption medium according to the invention, it is particularly suitable for removing acid gases from oxygen-comprising fluid streams. The oxygen content of such fluid streams is customarily 0.01 to 15% by volume, preferably 0.1 to 10% by volume.

The oxygen-comprising fluid stream is, e.g. a gas stream which is formed by oxidation of organic substances. The oxidation can be carried out with appearance of flames, i.e. as conventional combustion, or as oxidation without appearance of flames, e.g. in the form of a catalytic oxidation or partial oxidation. Organic substances which are subjected to the combustion are customarily fossil fuels such as coal, natural gas, petroleum, gasoline, diesel, raffinates or kerosene, biodiesel or waste materials having a content of organic substances. Feedstocks of the catalytic (partial) oxidation are, e.g. methanol or methane, which can be reacted to form formic acid or formaldehyde. The combustion of the organic substances proceeds mostly in customary combustion plants with air.

Preferred oxygen-comprising fluid streams are combustion exhaust gases.

The process is also suitable for the treatment of exhaust gases of fuel cells or chemical synthesis plants which make use of a (partial) oxidation of organic substances.

The process or absorption medium according to the invention is, in addition, suitable for treating hydrocarbonaceous fluid streams. The resultant hydrocarbons are, e.g., aliphatic hydrocarbons, such as $C_1$-$C_4$-hydrocarbons, such as methane, unsaturated hydrocarbons, such as ethylene or propylene, or aromatic hydrocarbons, such as benzene, toluene or xylene.

A hydrocarbonaceous fluid stream which can be treated using the absorption medium according to the invention is biogas. Biogas is a combustible gas which is produced from biomass by fermentation, i.e. essentially anaerobic decomposition.

The typical process of breakdown of organic material to form biogas comprises essentially four stages. In the first stage (hydrolysis), aerobic bacteria convert the high-molecular-weight organic substances (protein, carbohydrates, fat, cellulose) using enzymes into low-molecular-weight compounds such as simple sugars, amino acids, fatty acids and water. The enzymes which are secreted by the hydrolytic bacteria adhere to the outside of the bacteria (what are termed exoenzymes) and cleave the organic components of the substrate hydrolytically into small water-soluble molecules. In the second stage (acidification), the individual molecules are broken down and converted intracellularly by acid-forming bacteria. These are facultatively aerobic species which substantially consume the oxygen which is still remaining and thus provide the anaerobic conditions required for the methane bacteria. Here, principally short-chain fatty acids, low-molecular-weight alcohols and gases are generated. In the third stage (acetic acid formation), Acetobacteraceae produce the feedstocks for the methane formation (acetic acid, carbon dioxide and hydrogen) from the organic acids. In the fourth stage (methane formation), methane bacteria form the methane.

Before the workup, biogas is a gas mixture having the main components methane and carbon dioxide. Nitrogen, oxygen, hydrogen sulfide, hydrogen and ammonia are usually also present in small amounts. A typical composition of biogas is: methane 45-70% by volume, carbon dioxide 25-55% by volume, steam 0-10% by volume. nitrogen 0.01-5% by volume, oxygen 0.01-2% by volume, hydrogen 0-1% by volume, ammonia 0.01-2.5 mg/m$^3$, hydrogen sulfide 10-10 000 mg/m$^3$. Owing to the outstanding resistance of the absorption medium according to the invention towards oxygen, it is particularly suitable for the removal of acid gases from biogas having a content of oxygen, for example an oxygen content from 0.01 to 2% by volume.

The biomass used is customarily stable manure, straw, liquid manure, sewage sludge, fermentation residues and the like. Starchy grains or seeds also come into consideration. Bacterial decomposition proceeds, e.g., in customary biogas plants. A biogas reactor can be charged continuously or discontinuously. In the case of the discontinuous charging, what is termed the batch principle, the entire rotting vessel is filled at once. The batch rots without change of substrate until the end of the chosen residence time. The gas production starts after the vessel is filled, reaches a maximum and then plateaus. After the expiry of the residence time, the vessel is completely emptied apart from a residue acting as inoculation material for the next batch. The non-uniform gas production can be compensated for by a plurality of relatively small fermenters which are charged in staggered phases. A plurality of relatively small vessels, however, cause higher specific costs. Fermenters which are charged continuously with the materials to be fermented are advantageous, wherein at the same time a corresponding amount of rotted substrate is pumped off. As a result, a rotting which takes place permanently is achieved with constant gas production and, in addition, acidification is prevented due to the frequent addition of small amounts of substrate.

In addition, the process according to the invention can of course also be used in order to treat unburnt fossil gases, such as natural gas, e.g. what are termed coal seam gases, i.e. gases occurring in the extraction of coal, which are collected and compressed.

Devices suitable for carrying out the process according to the invention comprise at least one scrubbing column, e.g. packed columns, arranged-packing columns and tray columns, and/or other absorbers such as membrane contactors, radial-flow scrubbers, jet scrubbers, venturi scrubbers and rotary spray scrubbers. The gas stream is treated with the absorption medium preferably in a scrubbing column in countercurrent flow. The gas stream is generally fed into the lower region of the column and the absorption medium into the upper region of the column.

The temperature of the absorption medium is generally about 30 to 70° C. in the absorption step, when a column is used, for example 30 to 60° C. at the top of the column and 40 to 70° C. at the bottom of the column. A product gas (by-product gas) low in acid gas components, i.e. a product gas depleted in these components. and an absorption medium loaded with acid gas components are obtained.

The process according to the invention is particularly suitable for treatment of fluid streams which occur at a pressure close to atmospheric pressure, such as; e.g. combustion exhaust gases or biogas, and are not significantly compressed for treatment. Owing to the low vapor pressure of the absorption medium, no significant amounts of absorption medium components transfer to the treated fluid stream and scrubbing of the treated fluid stream is not necessary. In preferred embodiments, the fluid stream is contacted with the absorption medium at a pressure of 1.0 to 3.0 bar (absolute pressure).

The carbon dioxide can be released in a regeneration step from the absorption medium which is loaded with the acid gas components, wherein a regenerated absorption medium is obtained. In the regeneration step the loading of the absorption medium is reduced and the resultant regenerated absorption medium is preferably subsequently recirculated to the absorption step.

Generally, the loaded absorption medium is regenerated by
a) heating, for example from 70 to 130° C.,
b) expansion,
c) stripping with an inert fluid
or a combination of two or all of these measures.

Generally, the loaded absorption medium is heated for regeneration and the carbon dioxide released is separated off, e.g. in a desorption column. Before the regenerated absorption medium is again introduced into the absorber, it is cooled to a suitable absorption temperature. In order to exploit the energy present in the hot regenerated absorption medium, it is preferred to preheat the loaded absorption medium from the absorber by heat exchange with the hot regenerated absorption medium. By means of the heat exchange the loaded absorption medium is brought to a higher temperature so that in the regeneration step a lower energy usage is required. By means of the heat exchange, partial regeneration of the loaded absorption medium can also already proceed with release of carbon dioxide. The resultant gas-liquid mixed phase stream is passed into a phase separation vessel from which the carbon dioxide is taken off; the liquid phase, for complete regeneration of the absorption medium, is passed into the desorption column.

The invention will be described in more detail with reference to the accompanying figure and the example hereinafter.

FIG. 1 is a schematic depiction of a plant suitable for carrying out the process according to the invention.

According to FIG. 1, via a feed line 1, a suitably pretreated carbon dioxide-comprising combustion gas is contacted in countercurrent in an absorber 3 with the regenerated absorption medium which is fed via the absorption medium line 5. The absorption medium removes carbon dioxide by absorption from the combustion gas; a pure gas low in carbon dioxide is obtained via an exhaust gas line 7. Via an absorption medium line 9 and a throttle valve 11 the absorption medium which is loaded with carbon dioxide is passed to a desorption column 13. In the lower part of the desorption column 13, the loaded absorption medium is heated and regenerated by means of a heater (which is not shown). The carbon dioxide which is released in this process leaves the desorption column 13 via the exhaust gas line 15. The regenerated absorption medium is subsequently fed back to the absorption column 3 by means of a pump 17 via a heat exchanger 19.

EXAMPLE

A comparative absorption medium comprised an aqueous solution of potassium N,N-dimethylglycinate (7 mol %) and piperazine (2 mol %). A solvent according to the invention comprised an aqueous solution of potassium N,N-dimethylglycinate (7 mol %) and N-hydroxyethylpiperazine (2 mol %). Both absorption media were subjected to the following stress test: The aqueous absorption medium was charged into a glass flask.

The glass flask was heated from beneath and held at boiling temperature 100° C. A gas cooler is mounted on the glass flask which cools the gas phase to about 4° C. The amine phase which is present in the gas stream precipitates in the liquid phase and flows back to the glass flask. Via a further inlet to the glass flask, a mixed gas stream of 10 liter/h, comprising 9 parts of air and one part of $CO_2$ is introduced into the solvent.

After the 28th day, aliquots of the absorption medium were taken off and the content of piperazine or N-hydroxyethylpiperazine was determined by gas-chromatographic analysis. The recovery rates of piperazine or N-hydroxyethylpiperazine are shown in the table hereinafter. It is seen that piperazine is much more severely broken down in the course of the test than N-hydroxyethylpiperazine which is recovered virtually completely even after 4 weeks. N-Hydroxyethylpiperazine shows scarcely measurable breakdown in the presence of oxygen.

TABLE

Recovery rates of piperazine or N-hydroxyethylpiperazine

| Recovery of the activator in the stress test | Start of the stress test $C_{0\ days}$ [%] | After 28 days of stress test $C_{28\ days}$ [%] |
|---|---|---|
| Piperazine | 100 | 94 |
| N-Hydroxyethyl-piperazine | 100 | 99 |

The invention claimed is:

1. An absorption medium comprising an aqueous solution
(A) of an alkali metal salt of an N,N-di-$C_1$-$C_4$-alkylaminocarboxylic acid and
(B) N-hydroxyethylpiperazine.

2. The absorption medium according to claim 1, wherein the aqueous solution comprises 2 to 5 kmol/m³ of alkali metal salt of the N,N-di-$C_1$-$C_4$-alkylaminocarboxylic acid and 0.1 to 1.5 kmol/m³ of N-hydroxyethylpiperazine.

3. The absorption medium according to claim 1, wherein the alkali metal salt of the N,N-di-$C_1$-$C_4$-alkylaminocarboxylic acid is potassium N,N-dimethylglycinate.

4. The absorption medium according to claim 2, wherein the alkali metal salt of the N,N-di-$C_1$-$C_4$-alkylaminocarboxylic acid is potassium N,N-dimethylglycinate.

5. A process for removing acid gases from a fluid stream, in which the fluid stream is contacted with an absorption medium according to claim 1.

6. The process according to claim 5, wherein the fluid stream is oxygen-comprising.

7. The process according to claim 6, wherein the fluid stream originates from the oxidation of organic substances.

8. The process according to claim 5, wherein the fluid stream is obtained by essentially anaerobic decomposition of biomass.

9. A process for removing acid gases from a fluid stream, in which the fluid stream is contacted with an absorption medium according to claim 2.

10. The process according to claim 9, wherein the fluid stream is oxygen-comprising.

11. The process according to claim 10, wherein the fluid stream originates from oxidation of organic substances.

12. The process according to claim 9, wherein the fluid stream is obtained by essentially anaerobic decomposition of biomass.

13. A process for removing acid gases from a fluid stream, in which the fluid stream is contacted with an absorption medium according to claim 3.

14. The process according to claim 10, wherein the fluid stream is oxygen-comprising.

15. The process according to claim 14, wherein the fluid stream originates from the oxidation of organic substances.

16. A process for removing acid gases from a fluid stream, in which the fluid stream is contacted with an absorption medium according to claim 4.

17. A process for removing acid gases from a fluid stream, in which the fluid stream is contacted with an absorption medium according to claim 1 to obtain a fluid stream from which the acid gases have been removed and an absorption medium loaded with acid gas components.

18. The process according to claim 17, wherein the fluid stream is oxygen-comprising.

19. The process according to claim 18, wherein the fluid stream originates from oxidation of organic substances.

20. The process according to claim 17, wherein the fluid stream is obtained by essentially anaerobic decomposition of biomass.

21. The process according to claim 17, wherein the loaded absorption medium is regenerated by
    a) heating,
    b) expansion,
    c) stripping with an inert fluid
    or a combination of two or all of these measures.

22. The process according to claim 18, wherein the loaded absorption medium is regenerated by
    a) heating,
    b) expansion,
    c) stripping with an inert fluid
    or a combination of two or all of these measures.

23. The process according to claim 19, wherein the loaded absorption medium is regenerated by
    a) heating,
    b) expansion,
    c) stripping with an inert fluid
    or a combination of two or all of these measures.

24. The process according to claim 20, wherein the loaded absorption medium is regenerated by
    a) heating,
    b) expansion,
    c) stripping with an inert fluid
    or a combination of two or all of these measures.

* * * * *